United States Patent [19]

Delfort et al.

[11] Patent Number: 5,536,424
[45] Date of Patent: Jul. 16, 1996

[54] SULFONATED BISMUTH COMPOUNDS

[75] Inventors: Bruno Delfort, Paris; Maurice Born, Nanterre; Bertrand Daoudal, Pontigny; Jacques Lallement, Aubervilliers, all of France

[73] Assignee: Institute Francais Du Petrole, France

[21] Appl. No.: 378,375

[22] Filed: Jan. 25, 1995

[30] Foreign Application Priority Data

Jan. 26, 1994 [FR] France .................................. 94 00928
Mar. 3, 1994 [FR] France .................................. 94 02574

[51] Int. Cl.$^6$ ................................................ C10M 135/10
[52] U.S. Cl. ............................. 508/401; 252/353; 556/69; 556/76; 508/418
[58] Field of Search .......................... 252/33, 49.7, 353; 556/69, 76; C10M 135/10

[56] References Cited

U.S. PATENT DOCUMENTS 3,929,650 12/1975 King et al. ............................ 252/33 X
4,198,317 4/1980 Bertus et al. ........................ 556/69 X

OTHER PUBLICATIONS

Kapoor, Pratibha. "Preparation and Characterization of para--toluenesulphonato complexes of arsenic (III), antimony (III) and bismuth (III)". *Indian Journal of Chemistry*, 29A (Oct. 1990), 982–985.

*Primary Examiner*—Prince Willis, Jr.
*Assistant Examiner*—Cephia D. Toomer

*Attorney, Agent, or Firm*—Pollock, Vande Sande & Priddy

[57] ABSTRACT

New sulfonated bismuth compounds and the preparation thereof are described. These new compounds can be represented by the following general formulae:

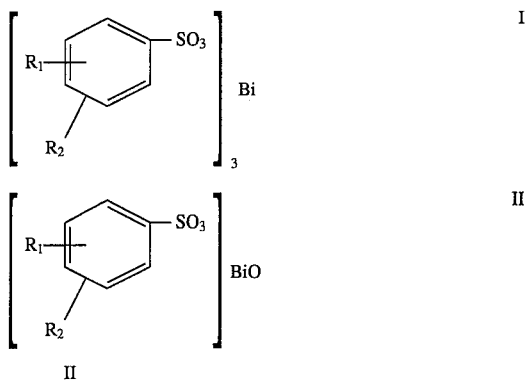

where $R_1$ represents a monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon. These compounds, which possess surface-active and wear-fighting properties, are used as fuel additives. They can also serve as starting materials in the manufacture of overbased colloidal products usable as lubricant additives by carbonation of at least one calcium, barium, or magnesium oxide or hydroxide, the carbonate formed being kept as a colloidal dispersion in an organic medium by using at least one of the sulfonated bismuth compounds (I) and (II).

20 Claims, No Drawings

SULFONATED BISMUTH COMPOUNDS

The invention concerns new bismuth sulfonate compounds and the preparation and use thereof.

It may prove advantageous in various applications to use "overbased sulfonate"-type products incorporating bismuth.

To date, these colloidal products have been composed essentially of a main portion comprising calcium or magnesium carbonate (and even calcium borate) kept in colloidal suspension by means of a surface-active agent normally consisting of an alkylaryl sulfonate of the same metal, i.e., calcium or magnesium, and, in some cases, of sodium or potassium.

New alkylaryl sulfonate bismuth compounds have now been discovered. These compounds possess surface-active properties and can be used, in particular, as starting materials in the manufacture of colloidal products.

The preparation of certain bismuth sulfonates has been previously described in the *Indian Journal of Chemistry*, Vol. 29, A 982–985 (1990). This article describes paratoluene bismuth sulfonates prepared in polar solvents such as nitromethane, acetonitrile or diethyl ether. The authors describe the preparation of an $(RSO_3)_3Bi$ bismuth sulfonate using one of the following reaction processes:

(1) $3RSO_3Ag + BiCl_3 \rightarrow (RSO_3)_3Bi + 3AgCl$ and

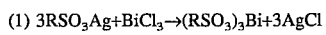

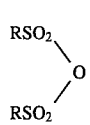

followed by:

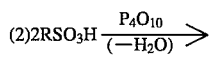

$2(RSO_3)_3Bi$

They also describe the preparation of an $RSO_3BiO$ bismuth compound by implementing the reaction:

$2RSO_3H + Bi_2O_3 \rightarrow 2RSO_3BiO + H_2O$ (in the formulae given above, R represents a paratolyl radical

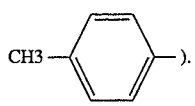).

The products in question are insoluble in hydrocarbons and have no surface-active properties (they do not have an HLB, i.e., Hydrophilic-Lipophilic Balance).

It has now been discovered that, beginning with the same starting sulfonic compound, it is possible to obtain selectively products whose structures are similar to those of bismuth sulfonates according to prior art, but which are soluble in hydrocarbons, possess surface-active properties, and can be used, in particular, as fuel and lubricant additives. They may also serve as intermediate products for the preparation of colloidal substances usable as lubricant additives.

The products according to the invention are prepared using methods not comparable to those described in prior art. These products, and the methods used to prepare them, fall within the scope of the invention.

The sulfonated bismuth compounds according to the invention are characterized by the fact that they correspond to one of the following formulae:

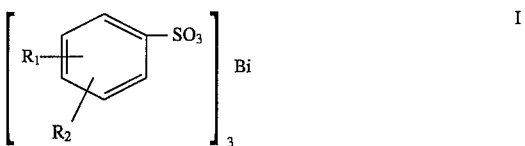

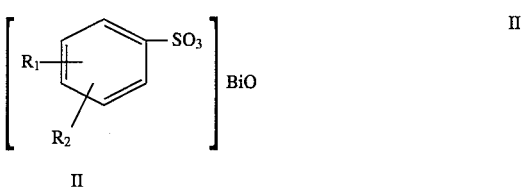

where $R_1$ represents a linear or branched monovalent aliphatic hydrocarbonaceous radical containing 8 to 36 atoms of carbon, and $R_2$ is represents an atom of hydrogen or a monovalent linear or branched hydrocarbonaceous radical containing 8 to 36 atoms of carbon.

The following might represent a single formula encompassing the general formulae (I) and (II) corresponding to the products according to the invention:

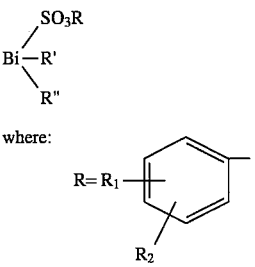

R' and R" may each be $RSO_3$, in which case formula (I), above, is applicable; or R' and R" may both represent an atom of oxygen, in which case formula (II) is applicable.

The operating procedures allowing selective preparation of the products corresponding to general formulae (I) and (II) from the same sulfonic acid $RSO_3H$ are distinguished mainly by the fact that, as regards the product corresponding to general formula (I), the reaction water formed during the procedure is removed, while, in the case of the product corresponding to general formula (II), water is present during the procedure.

The process for preparation of sulfonated bismuth compounds according to the invention comprises the reaction of at least one sulfonic acid corresponding to the general formula:

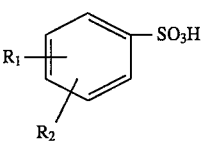

with bismuth oxide $Bi_2O_3$.

Sulfonic acid is normally used in solution in an aromatic aliphatic or cycloaliphatic hydrocarbonaceous solvent, which may be replaced by halogens (for example, toluene, xylene, chlorobenzene, or cyclohexane).

The molar proportion of bismuth oxide used is normally ⅙ to ⅔ in relation to the sulfonic acid. The reaction is carried out in the presence or absence of water.

If no water is present, preparation of a sulfonated bismuth compound according to general formula (I) may entail adding to the reactive mixture a light aliphatic monohydric alcohol containing, for example, 1 to 6 atoms of carbon, most often methanol. The mixture is then heated to remove any aliphatic monohydric alcohol present, and heating is continued, for example, to the reflux temperature of the hydrocarbonaceous solvent, normally at a temperature greater than 100° C. for ½ to 5 hours, for example.

The water is removed during the reaction, generally by heteroazeotropic distillation, or in the presence of an anhydride such as acetic anhydride. The reactive mixture is then normally allowed to cool, any solid products are separated out, e.g., by filtration, and the solvent is evaporated under reduced pressure.

In this case, the sulfonated bismuth compound corresponding to formula (I) is obtained.

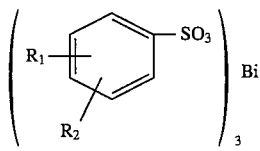    I

To prepare a sulfonated bismuth compound corresponding to general formula (II):

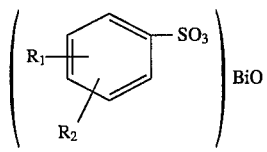    II the procedure is carried out in the presence of water. As described above, at least one sulfonic acid corresponding to general formula:

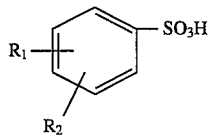

is reacted with bismuth oxide, normally in a mole ratio of ⅙ to ⅔ in relation to the sulfonic acid in an aromatic aliphatic or cycloaliphatic hydrocarbonaceous, potentially halogenated solvent. A quantity of water of up to about 50% by weight of the sulfonic acid and, potentially, a catalyst promoter comprising, for example, an aliphatic monohydric alcohol having 1 to 6 carbon atoms are added to the reactive mixture, which, during a first phase, is preferably kept at a temperature of below 100° C., i.e., 15 to 60 minutes, then heated to a temperature exceeding 100° C. for 30 minutes to 3 hours, for example.

The compounds according to the invention can be characterized by their bismuth content, which may reach approximately 25% by weight for products corresponding to general formula (I), and approximately 45% by weight for products corresponding to general formula (II), depending on the nature of the sulfonic acid used.

The compounds according to the invention have surface-active properties and may serve as surface-active agents in various applications. In particular, they may be used as additives in lubricating oils and in lead-free fuels, where they may produce an anti-recessive action on the valve seatings in internal combustion gasoline engines. They may also serve as starting materials in the manufacture of overbased colloidal products usable, in particular, as lubricant additives.

When used in this way, the aforementioned overbased colloidal products are prepared according to a process entailing carbonation by means of a carbonic anhydride and at least one calcium, barium, or magnesium oxide or hydroxide, the calcium, barium, or magnesium carbonate being kept in colloidal dispersion in an organic medium using a sulfonated bismuth compound corresponding to one of the general formulae:

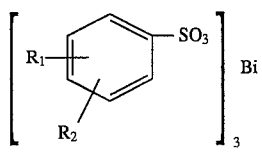    I or

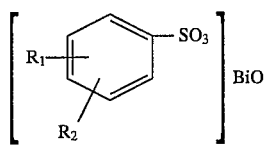    II in which $R_1$ represents a monovalent aliphatic linear or branched hydrocarbonaceous radical containing 8 to 36 atoms of carbon, and $R_2$ represents an atom of hydrogen or a monovalent aliphatic linear or branched hydrocarbonaceous radical containing 8 to 36 atoms of carbon. $R_1$ preferably represents a tetracosyl radical, and $R_2$, an atom of hydrogen.

The carbonation reaction is carried out using any conventional method for preparing overbased products, such as those described in U.S. Pat. Nos. 2,865,956, 3,150,088, 3,537,996, 3,830,739, 3,865,737, 4,148,740, 3,953,519, 3,966,621, and 4,505,830, and in French Patent No. 2,101, 813, by replacing the alkaline or alkaline-earth sulfonates normally used by the sulfonated bismuth compounds described above.

It should be noted that there are variants of the strong basification reaction which make use of carbonates preliminarily prepared from alkoxides and $CO_2$ before being placed in contact with the alkaline or alkaline-earth salt of the acid compound. These variants are described, most notably, in U.S. Pat. Nos. 2,956,018, 3,932,289, and 4,104,180.

The overbased colloidal products obtained from this application according to the invention are stable and soluble in mineral and synthetic lubricants.

They have a basicity reserve represented by the total base number (TBN), which may reach approximately 500 mg KOH/g; i.e., about 10 basic meq/g of product.

The bismuth content of these products way reach 40% by weight, and their calcium, barium, or magnesium content, approximately 20% by weight, for example.

The colloidal nature of these products is verified by dialysis through a latex membrane. Bismuth analyses locate this element in the undialyzed fraction (concentrate), which forms the colloidal part of the product.

The overbased colloidal compounds containing bismuth as obtained above are excellent wear-fighting and extreme-pressure additives, which are incorporated into lubricants when the latter are intended to lubricate components exposed to pronounced mechanical stresses, such as the valve-gear in thermal engines, gears, bearings, or stops. Sizable mechanical stresses are also generated during the machining of metals, both when cutting and forming.

Moreover, these overbased colloidal compounds containing bismuth possess a high degree of thermal stability, thereby allowing their use in lubricants subjected to very high temperatures of up to 160° C., as in some hard-running engine crankcases, transmissions bearing high loads, or in high-speed metal machining.

When using these products as additives for lubricating oils and for greases, they may be incorporated in the latter in a concentration of 0.1 to 25% by weight, and preferably 1 to 15% by weight.

Lubricating oils (or greases) also generally contain one or several additional additives, such as additives used to improve the viscosity index, additives intended to lower the pour point, antioxidants, anti-rust agents, copper corrosion-fighting additives, detergents, wear-fighting and anti-foaming agents, dispersing agents, and friction-reducing additives, with which the products according to the invention are compatible.

The following examples illustrate the preparation of sulfonated bismuth compounds according to the invention.

EXAMPLE 1

32.6 g (0.1 mole) dodecylbenzene sulfonic acid dissolved in 150 cm³ xylene were placed in a reaction vessel equipped with a stirring apparatus and a Dean and Stark separator. 23.3 g (0.05 mole) bismuth oxide $Bi_2O_3$, then 16 cm³ methanol were added. The medium was heated to the xylene-reflux temperature after draining off the methanol, and the medium was heated at this temperature for two hours. After cooling to ambient temperature, the medium was filtered, and the filtrate evaporated under reduced pressure. A homogeneous product containing 17.8% by weight of bismuth was obtained (theoretical value for $(C_{12}H_{25}-C_6H_4-SO_3)_3Bi=17.65\%$).

EXAMPLE 2

200 g alkylaryl sulfonic acid having a molar mass of 700 (or 0.286 acid equivalent) dissolved in 500 cm³ xylene were placed in a reaction vessel equipped with a stirring apparatus and a Dean and Stark separator. 68.0 g (0.146 mole) bismuth oxide $Bi_2O_3$, then 46 cm³ methanol were added. The medium was heated to the xylene-reflux temperature after draining off the methanol, and the medium was heated at this temperature for two hours. After cooling to ambient temperature, the medium was filtered, and the filtrate evaporated under reduced pressure. A homogeneous product containing 9.4% by weight of bismuth was obtained (theoretical value for $(R-SO_3)_3 = 9.1\%$).

EXAMPLE 3

32.6 g (0.1 mole) dodecylbenzene sulfonic acid dissolved in 150 cm³ xylene were placed in a reaction vessel equipped with a stirring apparatus and a Dean and Stark separator. 46.6 g (0.10 mole) bismuth oxide $Bi_2O_3$, 10.5 g (0.58 mole) water, then 56 cm³ (0.10 mole) methanol were then added. The medium was heated to 70° C. for two hours; then, after distillation of the methanol and water in the medium, the temperature thereof was kept at the xylene-reflux temperature for two hours. After cooling to ambient temperature, the medium was filtered, and the filtrate evaporated under reduced pressure. A homogeneous product containing 37.6% by weight of bismuth was obtained (theoretical value for $(C_{12}H_{25}-C_6H_4-SO_3)BiO=38.0\%$).

EXAMPLE 4

500 g of an alkylaryl sulfonic acid having an equivalent average molar mass of 700 (or 0.714 acid equivalent) dissolved in 800 cm³ xylene were placed in a reaction vessel equipped with a stirring apparatus and a Dean and Stark separator. 199 g (0.427 mole) bismuth oxide $Bi_2O_3$, 30.0 g (1.67 mole) water, then 162 cm³ methanol were then added. The medium was heated to 70° C. for two hours; then, after distillation of the methanol and water in the medium, the temperature thereof was kept at the xylene-reflux temperature for two hours. After cooling to ambient temperature, the medium was filtered, and the filtrate evaporated under reduced pressure. A homogeneous product containing 24.1% by weight of bismuth was obtained (theoretical value for $(RSO_3 BiO=22.6\%)$.

EXAMPLE 5

73.50 g of a bismuth alkylaryl sulfonate obtained as described in Example 2 containing 9.4% by weight bismuth dissolved in 219.9 g 130 Neutral mineral oil, 800 cm³ xylene, 30 cm³ methanol, 1.2 cm³ water, and 2.7 cm³ liquid ammonia were placed in a reaction vessel equipped with a stirring mechanism, a gaseous carbonic anhydride feed apparatus, and a thermometer. 67.80 g (0,916 mole) lime $Ca(OH)_2$ were dispersed in this solution and, while stirring vigorously, 32.3 g (0.733 mole) gaseous carbonic anhydride were bubbled into this solution over 40 minutes at a temperature of at most 45° C. After decantation and elimination of the higher hydroalcoholic phase, the lower phase was filtered and the solvents evaporated under reduced pressure. A homogeneous liquid product having the following characteristics was obtained: Alkaline reserve=3.46 basic meq/g; total base number (TBN)=194 KOH/g Bi=2.45% by weight Ca=7.50% by weight active substance: 39.2% by weight oil=60.8% by weight

EXAMPLE 6

74.20 g of a bismuth alkylaryl sulfonate containing 24.1% by weight bismuth obtained as described in Example 4 dissolved in 166.9 g 130 Neutral mineral oil, 800 cm³ xylene, 30 cm³ methanol, 1.3 cm³ water, and 2.6 cm³ liquid ammonia were placed in a reaction vessel equipped with a stirring mechanism, a gaseous carbonic anhydride feed apparatus, and a thermometer. 34.3 g (0.464 mole) lime $Ca(OH)_2$ were dispersed in this solution and, while stirring vigorously, 16.3 g (0.371 mole) gaseous carbonic anhydride were bubbled into this solution over 40 minutes at a temperature of at most 45° C. After decantation and elimination of the higher hydroalcoholic phase, the lower phase was filtered and the solvents evaporated under reduced pressure. A homogeneous liquid product having the following characteristics was obtained: Alkaline reserve=2.17 basic meq/g; total base number (TBN)=122 KOH/g Bi=7.95% by weight Ca=4.50% by weight active substance: 40.5% by weight oil=59.5% by weight

EXAMPLE 7

Examination of the Products by Dialysis in Heptane Through a Latex Membrane

The products in Examples 5 and 6, above, underwent dialysis in solution in normal heptane through a latex membrane. For each test, the mass fraction which had dialyzed (dialysis product) and the mass fraction which had not dialyzed (concentrate) were determined, the latter constituting the colloidal part. The bismuth concentration was also determined for each fraction. The results are given in Table 1. Incorporation of the bismuth in the concentrates alone confirmed the colloidal nature of the products under consideration.

TABLE 1

| Product in | Product Examination by Dialysis | | | |
|---|---|---|---|---|
| | Concentrate | | Dialysis Product | |
| Example | % by weight | % Bi | % by weight | % Bi |
| 5 | 39.2 | 6.1 | 60.8 | 0 |
| 6 | 40.5 | 19.9 | 59.5 | 0 |

EXAMPLE 8

Evaluation of Wear-Fighting and Extreme Pressure Properties

The products in Examples 5 and 6 according to the invention were evaluated for their wear-fighting and extreme pressure properties in a 130 Neutral lubricant oil. Performance was evaluated on a four-ball machine in accordance with method ASTM D 2783. The results are given in Table 2.

TABLE 2

Evaluation of the Wear-Fighting and Extreme Pressure Properties of the Products Containing 7% Active Substance in 130 Neutral Oil

| Product in Example | Filler Metal Load (daN) |
|---|---|
| none | 126 |
| 5 | 220 |
| 6 | 220 |

We claim:

1. Sulfonated bismuth compound, wherein said compound corresponds to the general formula:

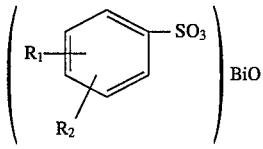

in which $R_1$ represents a monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon.

2. Compound according to claim 1, wherein, in formula (II), $R_1$ represents a dodecyl radical, and $R_2$ represents an atom of hydrogen.

3. Process for preparation of a sulfonated bismuth compound corresponding to formula (I)

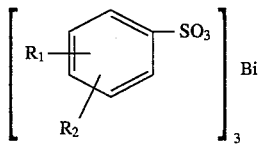

in which $R_1$ represents a monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon, wherein the process comprises reacting at least one sulfonic acid corresponding to the general formula:

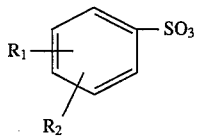

in which $R_1$ and $R_2$ are the same as in formula (I), in a solution of at least one solvent selected from the group consisting of a hydrocarbonaceous solvent, a halogenated hydrocarbonaceous solvent and mixtures thereof with bismuth oxide, $Bi_2O_3$; heating the reactive mixture, and separating out the sulfonated bismuth compound corresponding to formula (I).

4. Process according to claim 3, wherein the molar proportion of the bismuth oxide in relation to the sulfonic acid is ⅙ to ⅔.

5. Process according to claim 3 wherein said reactive mixture is heated to a temperature of more than 100° C.

6. Process according to claim 3, wherein an aliphatic monohydric alcohol containing 1 to 6 atoms of carbon is added as a catalyst promoter to the reactive mixture before heating.

7. Process for preparation of a sulfonated compound corresponding to formula (II)

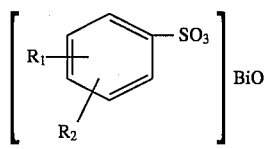

in which $R_1$ represents a monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon, wherein the process comprises reacting at least one sulfonic acid corresponding to the general formula:

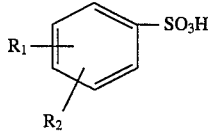

where $R_1$ and $R_2$ have the same meaning as in formula II, in a solution of at least one solvent selected from the group consisting of a hydrocarbonaceous solvent, a halogenated hydrocarbonaceous solvent and mixtures thereof with bismuth oxide, $Bi_2O_3$; adding water to the reactive mixture; heating the reactive mixture, and separating out the sulfonated bismuth compound corresponding to formula (II).

8. Process according to claim 7, wherein the molar proportion of the bismuth oxide in relation to the sulfonic acid is ⅙ to ⅔.

9. Process according to claim 7 wherein the reactive mixture is first heated to a temperature of less than 100° C., then to a temperature greater than 100° C.

10. Process according to any of claims 7 to 9, wherein an aliphatic monohydric alcohol having 1 to 6 atoms of carbon is added as a catalyst promoter to the reactive mixture before heating.

11. Composition containing as a surface-active agent, a sulfonated bismuth compound of claim 1.

12. A lubricating oil containing a sulfonated bismuth compound corresponding to one of the general formulae:

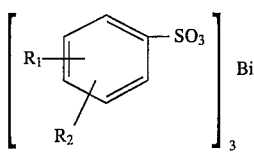

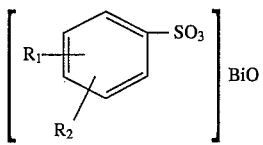

wherein $R_1$ represents monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon.

13. A process for preparing an overbased colloidal product which comprises carbonating at least one oxide or hydroxide of a member selected from the group consisting of calcium, barium, and magnesium to provide a carbonate of said at least one member; in the presence of at least one sulfonated bismuth compound corresponding to either of the general formula:

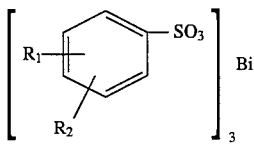

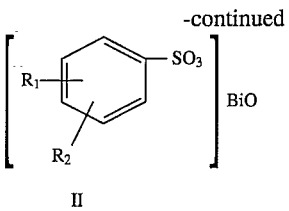

in which $R_1$ represents a monovalent linear or branched aliphatic hydrocarbonaceous radical containing 8 to 36 atoms of carbon, and $R_2$ represents an atom of hydrogen or a monovalent linear or branched aliphatic hydrocarbonaceous radical containing 8 to 36 atoms of carbon.

14. Overbased colloidal product obtained by the process according to claim 13.

15. Overbased colloidal product according to claim 14, wherein, in each of formulae (I) and (II) of the sulfonated bismuth compound, $R_1$ represents a tetracosyl radical and $R_2$ represents an atom of hydrogen.

16. Overbased colloidal product according to claim 14 wherein said product has an alkaline reserve as represented by a total base number of up to approximately 550 mg KOH/g of product (approximately 10 basic meq/g).

17. Overbased colloidal product according to claim 14 characterized by a bismuth content of up to approximately 40% by weight.

18. Overbased colloidal product according to claim 14 characterized by a calcium, barium, or magnesium content of up to approximately 20% by weight.

19. Lubricating oil or grease comprising as an additive the overbased colloidal product according to claim 14.

20. The lubricating oil or grease of claim 19 wherein the concentration of said colloidal product is from 0.1 to 25% weight.

* * * * *